United States Patent [19]
Rubinstein

[11] 3,955,574
[45] May 11, 1976

[54] PUMPING SYSTEM FOR CATHETER SUCTION UNITS

[76] Inventor: Morton K. Rubinstein, 14954 Corona Del Mar, Pacific Palisades, Calif. 90272

[22] Filed: Dec. 9, 1974

[21] Appl. No.: 531,179

[52] U.S. Cl. .............................. 128/278; 128/230
[51] Int. Cl.² ........................................... A61M 1/00
[58] Field of Search ............ 128/278, 276, 213, 214, 128/230; 137/205; 417/300, 36, 38

[56] References Cited
UNITED STATES PATENTS

| | | | |
|---|---|---|---|
| 3,429,313 | 2/1969 | Romanelli | 128/276 |
| 3,543,752 | 12/1970 | Hesse et al. | 128/230 X |
| 3,545,438 | 12/1970 | De Vries | 128/230 X |
| 3,620,215 | 11/1971 | Tysk et al. | 128/230 X |
| 3,693,613 | 9/1972 | Kelman | 128/278 |
| 3,709,222 | 1/1973 | De Vries | 128/230 X |
| 3,799,702 | 3/1974 | Weishaar | 128/278 |
| 3,812,855 | 5/1974 | Banko | 128/276 |
| 3,860,000 | 1/1975 | Wootten et al. | 128/276 X |

*Primary Examiner*—John D. Yasko
*Attorney, Agent, or Firm*—Eric T. S. Chung

[57] ABSTRACT

An improved pumping system for use with catheter suction units, is disclosed. A cyclical alternating of vacuum and pressure is applied to a catheter to have suction through the catheter interrupted by a predetermined period of blowing. A source of mist may be connected to the catheter to have a detergent or enzymatic fluid ejected through the catheter during selected periods of blowing.

17 Claims, 2 Drawing Figures

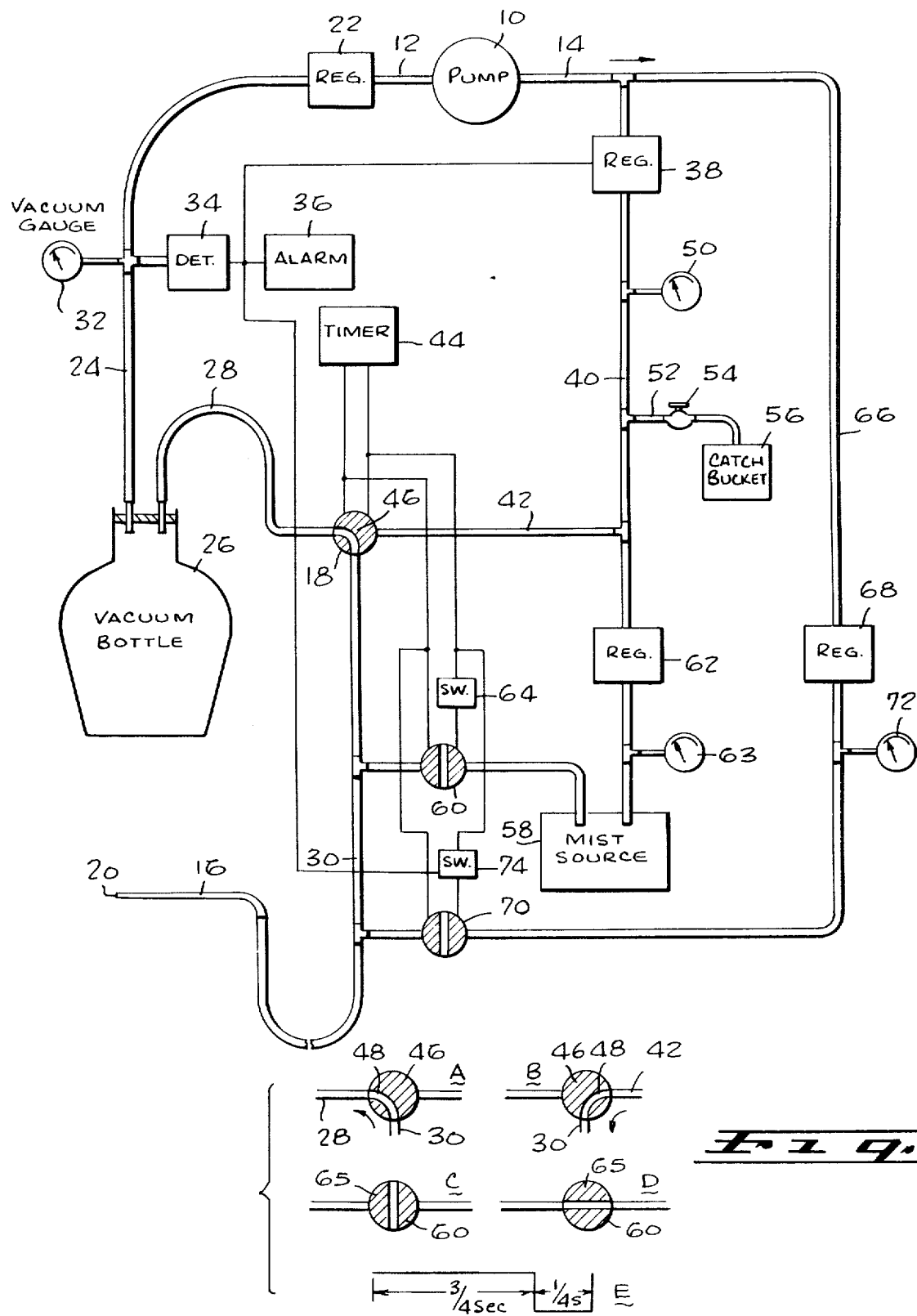

PUMPING SYSTEM FOR CATHETER SUCTION UNITS

BACKGROUND OF THE INVENTION

1. Field of the Invention

This invention generally relates to pumping systems that are used with catheters for drawing fluids and other viscous materials from a body, such as may be required during certain medical procedures. More specifically, the present invention concerns a pumping system wherein cyclical reversals of pumping pressure are applied to the catheter connected thereto to have negative and positive pressure cyclically alternated.

2. Description of the Prior Art

The use of catheter suction units for removing fluids and other viscous materials from a body is a conventional medical procedure.

Prior art suction units presently in use essentially involve a catheter to which is connected a suction pump for applying negative pressure thereto. Fluids in which the tip of the catheter is immersed are thereby drawn through the catheter into a vacuum bottle or other reservoir provided as a collector. Mucous membrane and viscous materials such as phlegm may also be drawn by such suction units. As may be expected, the tip of the catheter frequently becomes clogged by such viscous materials. Clearing normally requires that the catheter be withdrawn and washed in an appropriate solution. Suction is obviously halted during such cleaning procedure.

The drawing of mucous membrane into the catheter is further undesirable due to the resulting traumatic injury to mucosal surfaces from which mucous membrane is torn.

The problem of clogging and traumatic injury has been in the past sought to be solved by the design and use of catheters having more than a single aperture at its tip. As an example, a catheter presently being widely used includes a pair of apertures placed in the side walls near the tip of the catheter. The pair of side apertures ostensibly permits continuous suction through the catheter in the event that the tip aperture becomes clogged by mucous membrane or other globular materials that may be drawn. However, experience with the multi-aperture catheters has revealed that clogging is not prevented and suction efficiency is somewhat decreased due to the reduction in the suction vacuum by the side apertures. Further, the tearing of mucous membrane continues to be a problem.

It is accordingly the intention of the present invention to provide a pumping system for catheter suction units wherein the catheter is self-cleaning, the occurrance of traumatic injury due to the tearing of mucous membrane is reduced, and suction vacuum can be maximized by the use of a single-ended catheter. It is a further intention of the subject invention to provide a suction system which allows a mist of detergent, enzymatic fluid, or other fluids to be controllably ejected through the catheter to dissolve viscous materials such as phlegm to facilitate the suction thereof.

SUMMARY OF THE INVENTION

Briefly described, the present invention involves a pumping system for catheter suction units wherein suction and pressure are cyclically alternated to have the flow of fluid through a catheter cyclically reserved and thereby self-cleaning.

More particularly, the subject pumping system includes a time controlled valve which is operated at predetermined time intervals to have suction through the catheter interrupted by a predetermined period of positive pressure to cause a reversal of the fluid flow therethrough. A source of mist is connected to allow controlled injection of detergent or enzymatic fluid through the catheter. Extreme clogging of the catheter is remedied by a super-ejection mode during which bursts of positive pressure are applied to the catheter to blow free whatever materials are caught in the catheter and thereby eliminate the blockage.

BRIEF DESCRIPTION OF THE DRAWINGS

FIG. 1 is a schematic functional block diagram illustrating a pumping system for catheter suction units in accordance with the present inventon.

FIG. 2 is a series of graphic diagrams that are useful in understanding the operation of the subject invention.

DESCRIPTION OF THE PREFERRED EMBODIMENT

Referring to FIG. 1 of the drawings, a pumping system for catheter suction units in accordance with the present invention essentially includes a pump 10 for providing negative pressure at an inlet port 12 and positive pressure at an outlet port 14.

The negative pressure when applied to a catheter 16 via a valve 18 causes suction of fluids and other viscous materials situated at or in close proximity to a tip 20 of the catheter 16. As shown, the inlet port 12 of the pump 10 is connected to the catheter 16 via a vacuum regulator 22, tubing 24, a vacuum bottle 26, tubing 28, valve 18, and tubing 30. It is to be understood that all tubing referred to herein may be of any conventional and well known type that is readily available.

Fluids and other viscous materials drawn through the catheter 16, the tubing 30, the valve 18, and the tubing 28 during suction are deposited in the vacuum bottle 26 which is maintained under a predetermined vacuum. A vacuum gauge 32 may be connected to the tubing 24 to provide a visual indication of the vacuum level. The vacuum regulator 22 serves to enable control of the vacuum level and may be of any conventional type which permits adjustment of a range of vacuum levels. Typically, suction systems may involve negative pressures in the range of 0 to 25 inches of mercury.

Blockages of the catheter 16 cause an increase in vacuum level and hence may be readily detected by the use of a negative pressure or vacuum detector 34 which is connected to detect the vacuum level of the vacuum bottle 26 and activate an alarm 36 whenever the vacuum is increased beyond a predetermined level. The detector 34 and the alarm 36 may be any of the numerous conventional types available in the prior art.

Positive pressure provided at the outlet port 14 of the pump 10 may be provided to the catheter 16 via a pressure regulator 38, tubing 40 and 42, the valve 18, and the tubing 30, whenever the valve 18 is positioned to connect the tubing 42 to the tubing 30. Position control or switching of the valve 18 may be readily accomplished by use of a timer 44 having any conventional design. Similarly, any available conventional valve having at least three ports may be used. As an example, the valve 18 may be a Humphrey valve, Model 125-4E1 which is controlled by a recycling timer Model IFIS manufactured and sold by Minarik Electric Company, Los Angeles, Ca.

In order that negative pressure and positive pressure be alternately applied to the catheter 16, the valve 18 is controlled by the timer 44 to alternately connect tubing 28 to tubing 30 during a period of suction and connect tubing 42 to tubing 30 during a period of blowing. The flow of fluid through the catheter 16 is thereby cyclically reversed to produce a self-cleaning action as a result of the continuous back and forth movement of materials that may otherwise become wedged within the catheter 16 when moved in a single direction through the catheter 16. Such cyclical reversal of fluid flow through the catheter 16 has also been found to substantially reduce tearing of mucous membrane from mucosal surfaces that may come in contact with the tip 20 of the catheter 16, particularly when the tip of the catheter 16 is being moved about during a suction procedure. Any mucous membrane or other material just entering the tip 20 of the catheter will be blown free when positive pressure is applied to the catheter 16.

The valve 18 simply may involve a movable plug 46 having a connecting channel 48 and which is alternately rotated under the control of the timer 44 to have the channel 48 connect the tubing 30 to either the tubing 28 or the tubing 42 which would be connected to the standard parts of the valve 18. Referring to FIG. 2, diagram A illustrates the movable plug 46 of the valve 18 as being positioned to have the channel 48 permit fluid flow between the tubing 28 and the tubing 30 such that negative pressure is applied through the tubing 30 to the catheter 16. By comparison, diagram B illustrates the movable plug 46 as having been rotated to have the channel 48 positioned to permit fluid flow between the tubing 42 and the tubing 30 such that positive pressure is applied to the catheter 16 connected to the hose 30.

Any time periods can be employed for the periods of suction and blowing as well as for the total cycle by adjustment of the timer 44. However, where suction is the desired net effect, then the suction period preferably should be longer than the blowing period. It has been found that suction periods of three-fourths of a second interrupted by blowing periods of one-fourth of a second as illustrated by waveform E of FIG. 2, is highly effective to have net suction accomplished by the suction unit using a vacuum of approximately twenty inches of mercury and a positive pressure of five pounds per square inch. However, any cycle and ratio of negative to positive pressure can be used to satisfy a particular need.

The pressure regulator 38 may be of any conventional type wherein a range of positive pressure such as zero to 30 pounds per square inch may be adjusted for. A pressure gauge 50 may be connected to the tubing 40 to provide a visual indication of the positive pressure being applied through the tubing 40 to the catheter 16. Moisture is oftentimes transmitted through the pump 10 and the tubing used in a suction unit. It is desirable that such moisture be drained or bled from the system. To this end, a bleed line 52 having an appropriate stopcock 54 is provided to allow and control draining of moisture into a catch bucket 56, or the like.

The suction of certain viscous materials such as phlegm sometimes presents a problem which can be readily solved by applying a detergent or other enzymatic fluid that serves to break up or dissolve the phlegm and thereby facilitate the suction thereof. Such detergents or enzymatic fluids are typically applied as a mist by being injected into a body cavity from which suction is to take place. For this purpose, a mist source or container 58 for detergent, enzymatic fluid, or other fluid is connected via a valve 60 to the tubing 30 to have the detergent or other enzymatic fluid contained in the mist source 58 ejected through the catheter 16 whenever the valve 60 is operated to have the mist source 58 connected to the tubing 30.

The mist source 58 may be maintained under a normal pressure by being effectively connected to the outlet 14 of the pump 10 via a pressure regulator 62, the tubing 40, and the regulator 38. The regulator 62 would serve to provide reduced pressures to the source 58. A pressure gauge 63 may be used to provide a visual indication of the pressure at which the source 58 is maintained.

The valve 60 may be of the same type as the valve 46 except that only two parts would be required. Referring to FIG. 2, diagram C illustrates a movable plug 65 as being positioned to prohibit fluid flow through the valve 60. By comparison, diagram D illustrates the movable plug 65 as being positioned to allow fluid flow through the valve 60.

Referring once again to FIG. 1, the valve 60 is connected to be controlled by the timer 44 when electrically connected thereto via a switch 64. Accordingly, the valve 60 is operated, when actuated, in synchronization with the valve 46 such that the mist source 58 is connected to the tubing 30 via the valve 60 only during blowing periods when positive pressure is being provided to the catheter 16. The timer 44 must be adjusted to vary the ratio of times during which negative and positive pressures are applied from the pump 10 such that the net outflow rather than inflow, i.e., suction, occurs through the catheter 16.

As earlier mentioned, the subject catheter suction unit has been found to be essentially self-cleaning by reason of the cyclical reversal of fluid flow through the catheter 16. Nevertheless, to provide for those instances where blockage nevertheless occurs, bursts of positive pressure to effectively clear a blocked catheter 16 by blowing is accommodated by the provision of a tubing 66 connecting the outlet 14 of the pump 10 directly to the tubing 30 and the catheter 16 via a pressure regulator 68 and a valve 70. A gauge 72 may be connected to the tubing 66 to provide a visual indication of pressure used therein. The use of the extra tubing 66 eliminates the need for having to readjust the pressure regulator 38 to increase the positive pressure to a higher level that may be desired to blow a catheter 16 clear.

The valve 70, as shown, is also connected to be controlled by the timer 44 whenever a switch 74 is provided. The valve 70 may be of a type that is the same as the valve 60. As previously explained, with respect to the valve 60, the valve 70 would be operated by the timer 44 to connect the tubing 66 to the tubing 30 and the catheter 16 only during blowing periods.

Automatic application of the bursts of positive pressure via the regulator 68 and valve 70 may be readily accomplished by having the switch 74 connected by a lead 76 to the detector 34 to be operated in response to a blockage being detected. The alarm 36 would then also serve to indicate that clearing high positive pressure is being applied to the catheter 16.

As an addition or alternative, an automatic extra clearing mode of operation may be further provided for by having the regulator 38 be of a conventional type that is controlled to have a first positive pressure applied to the catheter 16 under normal operating conditions and controlled to have a higher clearing positive pressure applied to the catheter 16 whenever a blockage is detected. For this purpose, the detector 34 is again also connected to have the output signal thereof applied to control the regulator 38 as well as operate the alarm 36. Such a connection is illustrated by a lead 78.

It is now clear from the foregoing description that the subject invention provides a pumping system for a catheter suction unit that is essentially self-cleaning such that blockages of a catheter used therewith are substantially reduced, thereby allowing single aperture catheters having greater suction efficiency to be used. It is also now clear that the subject invention will decrease a tearing of mucous membrane from mucosal surfaces to thereby reduce traumatic injuries resulting therefrom. Further, the subject invention provides a quick and easy means for the ejection of detergent or enzymatic fluids to facilitate the suction of viscous materials.

While a preferred embodiment of the present invention has been described hereinabove, it is intended that all matter contained in the above description and shown in the accompanying drawings be interpreted as illustrative and not in a limiting sense and that all modifications which fall within the scope and spirit of the invention may be made.

What is claimed is:

1. A pumping system for a suction unit designed for suction of fluids and viscous materials from a human body, said pumping system comprising:
   pumping means for providing a source of positive pressure and a source of negative pressure;
   catheter means for drawing fluids and viscous materials therethrough in response to the application of negative pressure to said catheter means; and
   control means for alternately applying negative pressure and positive pressure, for predetermined periods of time, from said pumping means to said catheter means to produce suction of fluids and viscous materials through said catheter means when positioned in or on said fluids and viscous materials, the alternate application of negative pressure and positive pressure causing continuous cyclic reversals of fluid flow through said catheter means during said suction.

2. The pumping system defined by claim 1, said control means including:
   valve means having first and second positions for enabling application of negative pressure from said pumping means to said catheter means when in said first position and enabling application of positive pressure from said pumping means to said catheter means when in said second position; and
   timer means for operating said valve means to be alternately in said first and second positions thereof for predetermined time periods.

3. The pumping system defined by claim 1, further including:
   regulator means for regulating the positive and negative pressure being applied from said pumping means to said catheter means; and
   gauge means for providing a visual indication of said positive pressure and said negative pressure.

4. The pumping system defined by claim 1, further including:
   source means for containing a source of fluid desired to be ejected through said catheter means;
   source valve means for enabling said source means to be operatively connected to said catheter means to have fluid contained by said source means ejected through said catheter means; and
   switching means for controllably connecting said source valve means to said control means to have said source valve means operated to connect said source means to said catheter means only during selected periods during which positive pressure is being applied from sad pumping means to said catheter means.

5. The pumping system defined by claim 1, further including:
   detector means for providing a detector signal in response to the negative pressure applied to said catheter means exceeding a predetermined threshold; and
   alarm means responsive to said detector signal for providing an indication that said negative pressure applied to said catheter means has exceeded said predetermined threshold.

6. The pumping system defined by claim 1, further including reservoir means connected to have negative pressure applied thereto from said pumping means for receiving fluids and viscouse materials drawn through said catheter means.

7. The pumping system defined by claim 1, further including boosting means for controllably applying a predetermined secondary positive pressure from said pumping means to said catheter means, said boosting means having a secondary valve connected to said control means to enable said secondary positive pressure to be controllably applied to said catheter means only during selected periods when said positive pressure is being applied to said catheter means.

8. The pumping system defined by claim 2, further including:
   source means for containing a source of fluid desired to be ejected through said catheter means;
   source valve means for enabling said source means to be operatively connected to said catheter means to have fluid contained by said source means ejected through said catheter means; and
   switching means for controllably connecting said source valve means to said timer means to have said source valve means operated to connect said source means to said catheter means only during selected periods during which positive pressure is being applied from said pumping means to said catheter means.

9. The pumping system defined in claim 8, further including boosting means for controllably applying a predetermined secondary positive pressure from said pumping means to said catheter means, said boosting means having a secondary valve that is selectively connected to said timer means to enable said secondary positive pressure to be controllably applied to said catheter means only during selected periods when said positive pressure is being applied to said catheter means.

10. The pumping system defined by claim 9, further including:
    detector means for providing a detector signal in response to the incidence of negative pressures applied to said catheter means exceeding a predetermined threshold; and alarm means responsive to said detector signal for providing an indication that said negative pressures applied to said catheter means has exceeded said predetermined threshold.

11. The pumping system defined by claim 1, further including:
regulator means for regulating the positive and negative pressure being applied from said pumping means to said catheter means; and
gauge means for providing a visual indication of said positive pressure and said negative pressure.

12. The pumping system defined by claim 11, further including reservoir means connected to have negative pressure applied thereto from said pumping means for receiving fluids and viscous materials drawn through said catheter means.

13. The pumping system defined by claim 1, further including:
detector means for providing a detector signal in response to the negative pressure applied to said catheter means exceeding a predetermined threshold; and
regulator means for regulating the positive pressure applied from said pumping means to said catheter means, said regulator means being connected to receive said detector signal from said detector means, said regulator means applying to said catheter means a first positive pressure in the absence of a detector signal and a second positive pressure in response to the application of said detector signal.

14. The pumping system defined by claim 7, further including:
detector means for providing a detector signal in response to the negative pressure applied to said catheter means exceeding a predetermined threshold; and
switching means for controllably connecting said control means to said secondary valve, said switching means being connected to said detector means to be operated in response to said detector signal.

15. The pumping system defined by claim 14, said control means including:
valve means having first and second positions for enabling application of negative pressure from said pumping means to said catheter means when in said first position and enabling application of positive pressure from said pumping means to said catheter means when in said second position; and
timer means for operating said valve means to be alternately in said first and second positions thereof for predetermined time periods.

16. The pumping system defind by claim 15, further including:
regulator means for regulating the positive pressure applied from said pumping means to said catheter means, said regulator means being connected to receive said detector signal from said detector means, said regulator means applying to said catheter means a first positive pressure in the absence of a detector signal and a second positive pressure in response to the application of said detector signal.

17. The pumping system defined by claim 16, further including:
source means for containing a source of fluid desired to be ejected through said catheter means;
source valve means for enabling said source means to be operatively connected to said catheter means to have fluid contained by said source means ejected through said catheter means; and
switching means for controllably connecting said source valve means to said control means to have said sorcce valve means operated to connect said source means to said catheter means only during selected periods during which positive pressure is being applied from said pumping means to said catheter means.

* * * * *